US008025895B2

(12) United States Patent
Schilling et al.

(10) Patent No.: US 8,025,895 B2
(45) Date of Patent: Sep. 27, 2011

(54) PEST CONTROL AGENT, METHOD FOR MANUFACTURE OF PEST CONTROL AGENT, AND METHOD FOR PEST CONTROL

(75) Inventors: Kevin H. Schilling, Muscatine, IA (US); Richard E. Castle, Muscatine, IA (US); Sarjit Johal, Muscatine, IA (US); Frank W. Barresi, Muscatine, IA (US); Laura E. Chavez Flores, legal representative, Muscatine, IA (US)

(73) Assignee: Grain Processing Corporation, Muscatine, IA (US)

( * ) Notice: Subject to any disclaimer, the term of this patent is extended or adjusted under 35 U.S.C. 154(b) by 1072 days.

(21) Appl. No.: 11/330,413

(22) Filed: Jan. 10, 2006

(65) Prior Publication Data

US 2007/0160637 A1    Jul. 12, 2007

(51) Int. Cl.
*A01N 25/08* (2006.01)

(52) U.S. Cl. ......... 424/410; 424/408; 424/489; 514/919

(58) Field of Classification Search .................. 424/490, 424/408, 410, 489; 514/919
See application file for complete search history.

(56) References Cited

U.S. PATENT DOCUMENTS

| | | | | |
|---|---|---|---|---|
| 2,129,919 | A * | 9/1938 | File .............................. | 106/162.1 |
| 4,636,343 | A | 1/1987 | Shibanai | |
| 4,769,242 | A | 9/1988 | Shibanai | |
| 4,818,534 | A | 4/1989 | Levy | |
| 4,983,390 | A | 1/1991 | Levy | |
| 5,567,430 | A | 10/1996 | Levy | |
| 5,698,210 | A | 12/1997 | Levy | |
| 5,824,328 | A | 10/1998 | Levy | |
| 5,846,553 | A | 12/1998 | Levy | |
| 5,858,384 | A | 1/1999 | Levy | |
| 5,858,386 | A | 1/1999 | Levy | |
| 5,885,605 | A | 3/1999 | Levy | |
| 5,902,596 | A | 5/1999 | Levy | |
| 6,001,382 | A | 12/1999 | Levy | |
| 6,335,027 | B1 | 1/2002 | Levy | |
| 6,337,078 | B1 | 1/2002 | Levy | |
| 6,346,262 | B1 | 2/2002 | Levy | |
| 6,350,461 | B1 | 2/2002 | Levy | |
| 6,387,386 | B1 | 5/2002 | Levy | |
| 6,391,328 | B1 | 5/2002 | Levy | |
| 2003/0020043 | A1 * | 1/2003 | Barresi et al. .................. | 252/194 |
| 2005/0159315 | A1 * | 7/2005 | Doane et al. .................. | 504/360 |
| 2009/0269381 | A1 | 10/2009 | Schilling | |

FOREIGN PATENT DOCUMENTS

| | | |
|---|---|---|
| EP | 089588 | 9/1983 |
| EP | 0159631 | 10/1985 |
| EP | 0686399 | 12/1995 |
| EP | 1287739 | 3/2003 |
| FR | 2005448 | 12/1969 |
| WO | 8904842 | 6/1989 |
| WO | 9510184 | 4/1995 |
| WO | 9519376 | 7/1995 |

OTHER PUBLICATIONS

International Search Report and Written Opinion of ISR—Date Aug. 10, 2007 International application No. PCT/US2007/000051.
Search Report Annex in PCT/US2007/000051.

* cited by examiner

*Primary Examiner* — Johann Richter
*Assistant Examiner* — Andriae M Holt
(74) *Attorney, Agent, or Firm* — Fitch Even Tabin & Flannery

(57) ABSTRACT

Disclosed are a pest control agent, a method for preparing a pest control agent, and a method for controlling a pest. Generally, the pest control agent is formed by providing a porous starch and an active control agent absorbed within the porous starch, and compressing the porous starch in the presence of heat to form discrete plural particles. Preferably, one or more binders are employed, as are one or more secondary absorbents/fillers. In highly preferred embodiments of the invention, the pest control agent is prepared via pelletizing in a commercial pellet mill. The particles so prepared should be sufficiently durable to withstand bulk transport, such as by rail car or bag shipment. The particles should, however, release the control agent quickly upon contact with water, such that, for instance, the control agent may be released when the pest control agent is introduced to standing water. It is contemplated that the control agent is preferably a mosquito control agent.

4 Claims, No Drawings

PEST CONTROL AGENT, METHOD FOR MANUFACTURE OF PEST CONTROL AGENT, AND METHOD FOR PEST CONTROL

FIELD OF THE INVENTION

The invention is in the field of pest control agents. Preferred embodiments of the invention are in the field of mosquito control agents.

BACKGROUND OF THE INVENTION

Numerous pest control agents are known. Generally, pest control is accomplished by finding or devising a suitable active ingredient for control of the pest, and applying it to a pest controlled target area where it is desired to remove pests and/or to prevent the pest from developing. For instance, in the case of mosquito control, numerous oleogenous mosquito control agents have been developed. Certain mosquito control agents are composed of oleogenous nontoxic materials. It is known that mosquitoes develop in areas of standing water, and accordingly, such oleogenous pest control agents frequently are applied to the water to form a temporary barrier film on the surface of the water to thereby prevent or impede mosquito larvae from developing in or on the surface of the water.

Many conventional control agents are liquids. Such liquids are typically applied by spraying the liquid into a pest control target area. In many cases, it would be desirable to apply the pest control composition in solid form. Solid pest control compositions typically are less prone to volatile dissemination of the active agent, and in some instances may be more readily and conveniently applied; for example, solid pest control compositions may be dropped from a helicopter or airplane or other elevated conveyance onto the surface of a large body of water somewhat more readily than can liquids. In addition, solid control agents are believed to be more able to penetrate a vegetative canopy when disseminated from an elevated conveyance.

When it is desired to form a solid composition for mosquitoes, a number of criteria are desirable. First, the solid pest control composition should be sufficiently durable to allow the control composition to be transported in bulk, such as by rail car or via bagged transport. Second, the solid composition, which generally will include a carrier and an active control agent, must be compatible with the pest target area environment; consequently, the carrier should be readily biodegradable. Third, the solid pest control composition should readily and quickly release the control agent when applied into a water column or when otherwise contacted by water, such as rain. It has been observed that it is difficult to formulate a solid composition that is both sufficiently durable to withstand bulk transport and yet sufficiently capable of quickly releasing the active agent upon introduction to a water column.

The prior art has provided numerous efforts to devise such a pest control composition. For instance, U.S. Pat. No. 6,391,328 purports to describe a process for treating organisms with a composition that includes a carrier, an active ingredient, and a coating. The carrier material is said to include silica, cellulose, metal oxides, clays, paper, infusorial earth, slag, hydrophobic materials, polymers such as polyvinyl alcohol and the like. Control of the release of rate of the active ingredient is said to be obtained via choice of coating material, which is said to be a fatty acid, alcohol or ester. Similar technology purportedly is disclosed in U.S. Pat. Nos. 6,387,386; 6,350,461; 6,346,262; 6,337,078; 6,335,027; 6,001,382; 5,902,596; 5,885,605; 5,858,386; 5,858,384; 5,846,553 and 5,698,210 (all by Levy to Lee County Mosquito Control District, Fort Meyers, Fla.).

Another prior art effort at such a pest control composition is purportedly disclosed in U.S. Pat. Nos. 5,824,328, 5,567,430, 4,983,390 and 4,818,534. In accordance with the purported teaching of these patents, the activation is provided in the form of a material that includes a super absorbent polymer and inert diluents.

Generally, it is a goal of the present invention to provide a pest control composition. In preferred embodiments of the invention, the pest control composition is a mosquito control composition, and, in general, it is an object of these preferred embodiments to provide a composition that is sufficiently durable to withstand both transport but that is capable of releasing the active material quickly upon introduction to a water column. In other embodiments, it is a general goal of the invention to provide a method for preparing a pest control composition and a method for pest control.

THE INVENTION

It has now been discovered that a pest control composition may be prepared by sorbing a pest control agent into a porous granular starch. The porous granular starch is then compressed in the presence of heat, and preferably also in the presence of one or more binders and one or more fillers, to yield discrete plural particles of a pest control composition.

In preferred embodiments in the invention, the starch is a material that has been hydrolyzed to within a predetermined range surrounding an estimated optimum hydrolysis level for the selected control agent. In most cases, the optimum hydrolysis level is that hydrolysis level that which the absorption of the control agent is maximized. Most preferably, this material is introduced into a pellet mill with a binder and a filler that serves as a secondary absorbent for the control agent. The pellet mill is operated in a pelletizing operation to yield discrete plural particles which are in the form of pellets.

The method for pest control generally comprises introducing a pest control composition as described above into a pest target area.

Further features of the preferred embodiments of the invention are disclosed in more detail hereinbelow.

DETAILED DESCRIPTION OF THE PREFERRED EMBODIMENTS

The preferred embodiments of the invention are pest control compositions that compose a mosquito control agent and a carrier. The carrier is intended to allow release of the control agent upon contact with water, such as a lake or pond. The invention is not limited in scope to such embodiment, however. For instance, it is contemplated that the control agent may serve to mitigate against a waterborne pest, such as undesired marine life. In other embodiments, the control agent may be released in a nonaqueous environment, such as a land surface. In such cases, the composition may be designed to release the control agent upon contact with rain or ground moisture.

In accordance with the invention, the pest control composition includes a porous starch and a control agent, and in preferred embodiments further includes one or more binders, one or more fillers, and optionally other ingredients. The composition is in the form of discrete plural compacted particles. In preferred embodiments, the particles are pellets prepared using a commercial pellet mill.

Porous starches are described in detail in U.S. Pat. No. 6,946,148.

Generally, the invention contemplates the partial hydrolysis of a granular starch, preferably with an enzyme (enzyme catalysis). The starches that may be used as starting materials in preparing the porous starch granules may be derived from any native source, and typical starch sources include cereals, tubers, roots, legumes, and fruits. Exemplary starches include those obtained from corn, potato, wheat, rice, sago, tapioca, and sorghum. Corn starch is preferred in light of its low cost and ready availability, and also in light of the known skin affinity of corn starch and relative ease of modification of the granular structure of corn starch compared to starches such as potato. Suitable starches include pearl starches, such as PURE-DENT® B700 and corn starch B200, both sold by Grain Processing Corporation of Muscatine, Iowa. The starches used in conjunction with the invention not only may be native starches but also may be starches that have been modified prior to enzymatic hydrolysis (i.e. enzymatically catalyzed hydrolysis). Exemplary of such modified starches are cross-linked starches, which may comprise a native starch that have been cross-linked via any suitable cross-linking technique known in the art or otherwise found to be suitable in conjunction with the invention. An example of a commercially available cross-linked starch is PURE-DENT® B850, sold by Grain Processing Corporation of Muscatine, Iowa. Other starches are deemed suitable for use in conjunction with the invention, and thus, it is contemplated that, for instance, derivatized, or acid-thinned starches, or starches that have otherwise modified may be employed. Exemplary starches include PURE-SET® B950, PURE-GEL® B990, PURE-COTE® B790®, SUPERBOND® T300, SUPERCORE® S22, COATMASTER® K56F and starch C-165, all available from Grain Processing Corporation, Muscatine, Iowa.

In accordance with the invention, the starch is partially hydrolyzed, preferably with an enzyme. Suitable enzymes for using in conjunction with the invention include any of the wide variety of art-recognized enzymes suitable for hydrolyzing starch, and include, for instance, amylases derived from fungal, bacterial, higher plant, or animal origin. Preferred examples of suitable enzymes include endo-alpha-amylases, which cleave the 1-4 glucoside linkage of starch. In addition, the enzyme may include or comprise a beta-amylase, which removes maltose-units in a stepwise fashion from the non-reducing ends of the alpha 1-4 linkages; a glucoamylase, which remove glucose units in a stepwise manner from the non-reducing end of starch and which cleaves both 1-4 and the 1-6 linkages; and debranching enzymes such as isoamylase and pullulanase which cleave the 1-6 glucosidic linkages of the starch. Such enzymes can be used alone or in combination. More generally, any starch that hydrolyses granular starch via the porous starch granules may be employed in conjunction with the invention.

Preferred sources of alpha-amylases and pullulanases include several species of the *Bacillus* micro-organism, such as *Bacillus subtilis*, *Bacillus licheniformis*, *Bacillus coagulans*, *Bacillus amyloliquefaciens*, *Bacillus stearothermophilus*, and *Bacillus acidopullulyticlus*, preferably the thermal stable amylases produced by *Bacillus stearothermophilus*, *Bacillus*, *licheniformis*, and *Bacillus acidopullulyticus*. Maltogenic alpha-amylase, an enzyme that produces high quantities of maltose and low molecular weight saccharides, is produced in *Bacillus* species; this enzyme can be obtained from Novo Nordisk under the trademark MALTOGENASE™. Preferred glucoamylases include those obtained from strains from *Aspergillus niger*. One alpha-amylase suitable in conjunction with the invention is G995, an alpha-amylase enzyme that is commercially available from Enzyme Biosystems LTD. One glucoamylase that is suitable for use in conjunction with the invention is G990, sold by Enzyme Biosystems Ltd.

The starch should be partially hydrolyzed with the selected enzyme to yield a porous starch granule. Generally, the enzymatic hydrolysis is accomplished in an aqueous or buffered slurry at any suitable starch solids level, preferably a solids level ranging from about 10% to about 55% by weight on dry starch basis, more preferably about 25% to about 35% by weight. The pH and temperature of the slurry should be adjusted to any conditions effective to allow enzyme hydrolysis. These will vary depending on the enzyme and starch that are selected, and are not critical so long as the starch does not gelatinize; generally, this can be accomplished so long as the temperature remains below the gelatinization temperature of the starch. In general, the pH will range from about 3.5 to about 7.5, more preferably from about 4.0 to about 6.0. To reach this pH, any suitable acid or base may be added, or a buffer may be employed. The temperature preferably is maintained at least 3° C. below the gelatinization temperature of the starch. For corn starch, the gelatinization temperature falls within a range between about 62° and 72° C. Accordingly, the temperature of the slurry should be below about 62° C., preferably ranging from about 22° C. to about 59° C., and more preferably from about 51° C. to about 61° C.

The enzyme may be employed in any amount suitable to effectuate a partial hydrolysis of the starch granules in the slurry. Preferably, the enzyme is employed in the slurry in a concentration ranging from about 0.2% to about 3% by weight on dry starch, and more preferably from about 0.4% to about 2%. For glucoamylase, this range is based on a 300 unit per ml enzyme (based on the Enzyme Biosystems unit definition); for alpha-amylase, this range is based on a 2200-5000 unit/ml enzyme For the maltogenic alpha-amylase, the units are based on a commercial 4000 unit/ml enzyme (MALTOGENASE from Novo Nordisk).

When it is desired to terminate the enzymatic hydrolysis, the enzymatic hydrolysis may be terminated by any suitable techniques known in the art, including acid or base deactivation, ion exchange, solvent extraction, or other suitable techniques. Preferably, heat deactivation is not employed, since a granular starch product is desired and since the application of heat in an amount sufficient to terminate the enzymatic reaction may cause gelatinization of the starch. For typical enzymes, acid deactivation may be accomplished by lowering the pH to a value lower than 2.0 for at least 5 minutes, typically for 5 to 30 minutes. After deactivation, the pH of the slurry may be readjusted to the desired pH according to the intended end use of the granules. Typically, the pH will be adjusted to a pH within the range from about 5.0 to 7.0, more preferably from about 5.0 to about 6.0. The starch granules thus prepared then can be recovered using techniques known in the art, including filtration and centrifugation. Preferably, the reducing sugars and other byproducts produced during the enzymatic treatment are removed during the washing steps. Most preferably, the starch granules subsequently are dried to a moisture content of or below about 12%.

In other embodiments of the invention, the starch granules are hydrolyzed via acid hydrolysis without the use of an enzyme. In such embodiments, the starch is placed in an aqueous acid medium at a low pH (typically a pH below 2.0, and more preferably below 1.0) at an elevated temperature for a time sufficient to hydrolyze the starch. Those skilled in the art will appreciate that many reaction conditions may be employed. For instance, the hydrolysis time may range from a few hours to a period of days. Generally, the starch solids level and temperature should be within the ranges described above with respect to enzymatic hydrolysis. When it is desired to terminate the hydrolysis, the pH should be adjusted to a level sufficient to terminate substantially completely the hydrolysis (typically to a pH ranging from about 5-7). The starch is preferably dried, as discussed hereinabove. While this method is suitable for the hydrolysis of starch, use of an enzyme is preferred, inasmuch as it is believed such use will provide a degree of regional specificity of hydrolysis of the starch granule that will be lacking absent the use of an enzyme. It is further believed that the use of an enzyme will affect the absorption properties of the resulting porous starch granules. Also, enzyme catalysts allow operation at more moderate pH levels.

In some embodiments of the invention, two hydrolyses are performed; one an enzymatically catalyzed hydrolysis and one not catalyzed enzymatically. The hydrolyses may be performed in either order. Preferably, the first of the hydrolyses is terminated after the starch granule has been hydrolyzed to an extent of about 50% of the desired extent of hydrolysis and the second hydrolysis is next commenced and allowed to proceed to finish the hydrolysis to the desired extent. More generally, the first hydrolysis may be allowed to proceed from about 10% to about 90% of the desired extent.

In accordance with a preferred embodiment of the invention, the starch is hydrolyzed to an optimum hydrolysis level for the absorption of the intended active control agent to be sorbed within the starch. By "hydrolysis level" is contemplated the percentage of the starch granule that is enzymatically hydrolyzed and thus no longer remaining in granular form. The optimum fluid absorption hydrolysis level most preferably is determined empirically, that is, by testing the absorption properties for the control agent and for a specific starch hydrolyzed with the specific enzyme being contemplated at various hydrolysis levels, and estimating from this information the hydrolysis level that yields the optimum fluid absorption property. The hydrolysis level alternatively may be determined via reference to a predetermined correlation of fluid absorption levels and hydrolysis levels. If the optimum hydrolysis level is known in advance, the "determination" of the optimum hydrolysis level may be simply predetermining the hydrolysis level with reference or regard to the known optimum level. In any event, the extent of hydrolysis of starch in a given hydrolysis reaction may be determined or estimated from the reaction time.

The optimum absorption property is generally deemed to be the hydrolysis level at which the maximum amount of the control agent is employed. Where plural ingredients are combined to form the control agent (for instance, the control agent is composed of multiple active ingredients), the optimum absorption property is generally deemed to be the hydrolysis level at which the total amount of control agent is maximized. It is contemplated in some embodiments that a hydrolysis level that is different from this maximum level may be deemed "optimum."

The enzymatic or acid hydrolysis should be allowed to continue to within a selected range surrounding the estimated absorption optimum hydrolysis level. Any suitable range may be selected. For instance, once the fluid absorption optimum hydrolysis level has been estimated, the hydrolysis may be allowed to proceed to within ±15%, more preferably ±10% and even more preferably ±5%, of the estimated optimum level.

Once the fluid absorption optimum hydrolysis level has been determined, the starch is hydrolyzed with the enzyme to within the selected range surrounding the optimum level. The granules can be recovered using any suitable technique known in the art or otherwise found to be suitable, including filtration and centrifugation.

The absolute magnitude of the hydrolysis level of the starch is expected to vary depending on the control agent employed. Generally, it is contemplated that for many control agents, using corn starch, the optimum hydrolysis level may range from about 30% to about 50%, in some embodiments, about 30% to about 44%; in other embodiments; from about 35% to about 44%; in other embodiments from about 38% to about 42%; and in other embodiments the hydrolysis level may be about 40%. This optimum represents the lowest hydrolysis level at which oil absorption reaches an apparent plateau.

Any suitable control agent is useful in connection with the invention. The control agent may be any material intended to treat or ameliorate a pest, which may be any living entity. Exemplary pests are insects and other bugs (e.g., mosquitoes, bark beetles, sand flies, black flies, midges), or other animals (e.g., fish, barnacles, snails) or aquatic and wetland plants, and especially parasitic animals (e.g., nematodes, mollusks, protozoans, and bacteria) or floating or submersed nuisance weeds e.g., algae, duckweed, hydrilla, water hyacinth, chara, watermilfoil, cattail bass weed, burreed, coontail, and the various pondweeds including bushy, curly-leaf, flat stem, floating-leaf, horned, and sago; water star grass, arrowhead, bladderwort, bulrush, hornwort, creeping water primrose, pickerelweed, spatterdock, cow lily, yellow water lily, waterweed, water chestnut, water smart weed, white water lily, naiad, watershield, elodea, hydrollia, alligatorweed, cattails, giant cutgrass, guineagrass, knotgrass, maidencane, paragrass, phragmites, spatterdock, and torpedograss.

Any suitable control agents may be employed in the compositions of the present invention. For instance, a control agent intended to treat populations of adult or immature (e.g., egg, larvae, pupae, nymphs) organisms may be employed. Classes of ingredients deemed suitable include pesticides, insecticides, toxicants, surface films, petroleum oils, insect growth regulators, plant growth regulators, animal growth regulators, microbial control agents, antibiotics, bioactive control agents, bactericides, and viricides, fungicides, algaecides, herbicides, nematicides, amoebicides, acaricides, miticides, predicides, schistisomicides, molluscicides, larvicides, pupicides, ovicides, adulticides, nymphicides, and the like. Combinations of two or more materials may be employed.

When the control agent is an insecticide, the material may be one or more of malathion, resmethrin, dichlorvos, bendiocarb, fenitrothion and chlorpyrifos. Insecticides such as pyrethrin and pyrethroid can be effective as larvicides for mosquitoes. When the material is a herbicide, it may be a material such as AMITROLE®, ammonium sulfamate, BROMACIL®, copper salts, dalapon, DICHLORBENIL®., DIQUAT®., DIURON™, ENDOTHALL®, FENAC®, PICLORAM®, PROMETON®, SILVEX®, SIMAZINE®, trichloroacetic acid, 2,4-D, 2,4,5-T, VELPAR®, TSMA, dicamba, endothall, silvex, prometon, chlorate, sodium metaborate, monuron, and the like. When the control agent is a weed control agent, it may be, for instance, acrolein, an aromatic solvent (such as xylene), copper sulfate and other water soluble copper salts or compounds, dalapon, dichlorbenil, 2,4-D, diquat, endothall, glyphosate, simazine, or fluridone. When the composition is intended to be used in connection with mosquito control, the preferred control agent is an ethoxylated alcohol sold under the trademark AGNIQUE® MMF, sold by Cognis Corporation of Cincinnati, Ohio. AGNIQUE® is intended to create a monomolecular film at the surface of a still body of water, thereby impairing the ability of mosquitoes and midges to reproduce and grow. The ethoxylated alcohol forms a non-toxic, temporary physical air/water barrier at the surface of the water to thereby interrupt both larval and pupal development cycles of the mosquito.

More generally, when the material is intended to be applied to a water column to prevent the growth of pests at the surface of the water, the control agent is preferably oleogenous, by which is contemplated that the material is film-forming on the surface of the water.

The starch and control agent may be present in any suitable amounts relative to one another. Preferably, analyzing the starch on a dry solids basis, the ratio of starch control agent preferably is in the range of from 1.5:1 to 0.5:1, more preferably, 1.3:1 to 1:1. These ranges are intended as general guidelines, and it is contemplated that more or less control agent relative to starch may be employed if desired.

It is contemplated that the starch and control agent may be used together in a pest control composition with essentially no other ingredients present. However, in preferred embodiments of the invention, one or more fillers and one or more binders preferably are employed. The composition of the invention preferably has the following range of ingredients (in all cases the sum total is preferably 100%; i.e., it is preferred that no additional materials are employed):

| Ingredients | Preferred Range | Most Preferred Range |
| --- | --- | --- |
| Starch | 30 to 50% | 40 to 45% |
| Control agent | 30 to 50% | 35 to 40% |
| Binders | 5 to 15% | 8 to 12% |
| Fillers | 5 to 15% | 8 to 12% |
| Moisture | 5 to 10% | 5 to 10% |

Any suitable filler may be used in connection with the invention. The best performing compositions do not employ a filler (and thus somewhat greater amounts of starch and/or control agent may be employed than specified above). In practice, however, the filler is preferably present for a number of reasons. For instance, the filler can allow for adjustment of the relative amounts of the other ingredients, and can affect the formulation properties and manufacturing characteristics of the pellets. When used, the filler preferably is inexpensive relative to the starch and control agent. The preferred fillers are materials that act as secondary absorbents, i.e., that serve to assist in retaining the agent in the composition. One preferred filler is wheat middlings. Wheat middlings are a byproduct of the milling of wheat, and are composed of fine particles of wheat bran, shorts, germ, and flower. The primary composition of wheat middlings is approximately 18% protein, 24% fiber, 13% water, 4% fat, 6% minerals and 10% other organics such as acids and salts. Other suitable fillers include materials such as spent or virgin corn germ, ground corn hulls, corn gluten, corn meal, corn bran, wheat flour, rice hulls, soy hulls, diatomaceous earth, wood flour, saw dust, vermiculite, and bentonite. The identify and relative amounts of the filler may be selected as needed depending on the control agent and the desired characteristics of the pest control composition.

The pest control composition preferably further includes a binder. The function of the binder is to retain the cohesiveness of the final particles in final compressed form, such as a final pelleted form. Typical binders include materials such as lignins, sulfonated lignin compounds, other lignin derivatives, gums, protein compounds, gelatin, and molasses. The lignin compounds may be calcium, sodium, magnesium, or ammonium lignosulfonate salts. In many cases, it is preferred to use such binders, because such binders are readily biodegradable and naturally derived. However, in preferred embodiments in the invention, urea-based binders, such as urea-formaldehyde resins, are employed as a first binder, with one or more of the heretofore discussed naturally derived binders employed as a second binder. Urea-based binders have been found particularly effective for use in conjunction with the invention. It is believed that this is a result of an interaction between the granular starch present in the composition and urea, although the precise mechanism of action is not known with certainty. Moreover, use of two binders is preferred, because, by adjusting the ratio of two binders with different characteristics, it is possible to adjust the resulting overall characteristics of the pest control composition. It has been found easier to attain the proper and desired hardness and water release characteristics by adjusting the relative amounts of two separate binders, rather than attempting to formulate the pest control composition using a single binder.

To prepare the pest control composition, the ingredients of the composition are blended and compressed in the presence of heat, by which is contemplated in temperature of at least 35° C., and usually a greater temperature. Generally, it is preferred to blend all of the ingredients together in a single mixing step, using equipment such as a ribbon blender. If it is desired to blend the ingredients in stages, the starch first should be blended with the control agent to allow absorption of the control agent within the porous starch granules to form a starch/control agent composition. The starch/control agent composition then may be blended with the other ingredients. Heat preferably is applied in pelletizing operation, using equipment known in the art as a pellet mill (although other equipment may be employed). The ingredients that are to form the composition are introduced into a pellet mill in the presence of heat and sufficient moisture to allow for pelleting. Upon pelletizing, discrete plural particles of pest control composition will be provided.

Generally, the pellet mill may be operated under any suitable conditions. Preferably, steam is added. Steam supplies both heat and moisture to the mixture of ingredients. The total moisture in the pellet mill preferably is about 10-15% (including moisture that may be proposed in the starting materials). Moisture has been found useful in assisting with the binding of the pellets, and preferred temperatures have been found to be in the range of 180 to 190° F. (82 to 88° C.) before passage of the mixture through the mill die. At higher temperatures, processing problems may result.

The pellet mill is essentially an extruder in which the mixed ingredients exit the mill through a die which serves to compress the mix into a pellet. The cutter reduces the extrudate to pellets. The dimensions of the die determine the size of the resulting pellet. A typical die has a one/eighth in. diameter with an orifice length of one to two inches. Pellets made using such a die will be approximately one-eighth inch diameter and typically between one-eighth to three-eighth of an inch in length, possibly up to about one inch in length. Length is controlled by adjustment of the distance between the cutter and the die surface. Pellets of this size have been found to provide a good combination of ease of handling and proper rate of dispersion of control agent once applied to water. In practice, pelleted material may be passed through a screening unit to select a desired size distribution, and oversize and undersize product can be recycled.

In some embodiments of the invention, a final drying and/or heating and/or curing step may be employed. It has been found that such a final heating/drying/curing step can be omitted following the teachings of the present invention.

Omission of such step is deemed advantageous and preferred. Following the preferred embodiments of the invention, the moisture content of the pellets upon air drying is approximately 10% by weight.

As heretofore described, other ingredients preferably are not employed in the pest control composition of the invention. If desired, other ingredients may be added. Such other ingredients may be added in any amount suitable for the intended purpose of such ingredient.

A pest control composition prepared in accordance with the foregoing teachings may be applied to a desired pest targeted area. Preferably, the case of mosquito control, the pest target area will be an area of standing or slowly moving water, such as a pond or small lake. Other pest control compositions may be applied to any other desired pest target area.

It is contemplated that the pest control composition of the invention may be applied via elevated conveyance, such as helicopter or plane. In some embodiments, the solid composition is suitable for release from an elevated conveyance onto a vegetative canopy, such as a forest tree. A substantial portion of the pest control composition will drop below the tree line. In other embodiments, the pest control composition is applied via ground moving conveyance or by boat. It is contemplated that the pest control method includes both applying pest control composition to reduce the number of pests that are presently in a pest targeted area and applying pest control composition to impede or prevent the growth or development or introduction of pests into the pest target area.

Desirably, the discrete plural particles of pest control composition prepared in accordance with the present teachings should be sufficiently durable to withstand bulk transport, such as via rail car or via bagged transport. A determination as to whether the particles are sufficiently durable will be readily apparent to one of ordinary skill in the art. As a general guideline, the particles should have a crush strength of at least 500 grams, preferably at least 600 grams, when evaluated in accordance with the teachings set forth herein at Example 1. It is contemplated that particles of a different size likewise should have a crush strength of at least 500 grams, preferably 600 grams; it is believed, however, that differently sized particles may employ different minimum crush strengths. If the transport distance is not large, a smaller target crush strength (such as 300 grams, 400 grams, or any desired number) may be selected. Alternatively, one may evaluate the particles for friability. Friability may be determined by tumbling a known weight of pellets in an apparatus for said period of time and by determining the change at screen distribution before and after tumbling. Softer and more brittle pellets are readily broken into small fragments during the tumbling process, to thereby result in a greater proportion of smaller particles. If friability is the selected criterion, one of ordinary skill in the art may select specific testing conditions and standards suitable for the intended application.

Satisfactory release characteristics, or dispersibility, may be determined by measuring the length of time for the pellets to disintegrate in water and, for oleogenous control agents which are intended to form a film on the surface of the water, the time taken for such film to form. The suitability in any given application of a particular pellet with a particular release profile is a matter left to the discretion of one of skill in the art. In preferred embodiments, at least 50% of the control agent is released within 24 hours of the introduction of the pest control composition to a water column at 25° C. More preferably, at least 55% of the control agent is released; even more preferably, at least 60% is released; even more preferably, at least 65% is released, even more preferably, at least 70% is released; even more preferably, at least 75% is released; even more preferably, at least 80% is released; even more preferably, at least 85% is released; and even more preferably, at least 90% is released.

The following examples are provided to illustrate the invention, but should not be construed as limiting the invention in scope.

Example 1

A pest control composition having the following formulation was prepared (the following materials were provided "as is," and the weights provided included moisture):

| | | |
|---|---|---|
| Porous starch absorbent | 900 lbs | 45% |
| Ethoxylated alcohol active agent. | 700 lbs | 35% |
| Urea-formaldehyde resin binder | 100 lbs | 5% |
| Calcium lignosulfonate binder | 100 lbs | 5% |
| Wheat middlings | 200 lbs | 10% |

These materials were blended in a single mixing step and introduced to a production scale California pellet mill. Steam was added to bring the temperature to between 180°-190° F. The product was pelletized through ⅛ inch die to form cylindrical pellets. The pellets were allowed to air dry. The resulting cylindrical pellets were ⅛ of an inch in diameter and ¼ inch long.

The particles were subjected to a crush strength test in accordance with the following procedure:

Crush strength was measured using a TA-XT2 Texture Analyzer (Texture Technologies, Scarsdale, N.Y.) at room temperature and ambient humidity. A pellet was placed on the stage of the TA-XT2. The analyzer was programmed to compress the pellet with an aluminum cylinder having a diameter of ¼ inch. The cylinder was programmed to travel 3 mm after touching the surface of the pellet (trigger force 25 gram) at the speed of 1.0 mm/second. The force of compression was measured and recorded in grams during the course of the compression, with force and resistance to compression increasing over time. Eventually, the pellet cracked and broke, resulting in a decrease or "yield" in the force of compression. The crush strength for a given pellet was the force of compression, in grams, at the time of breakup of the pellet. For any given sample formulation, this was repeated at least ten times on ten different pellets from the same batch, and the average of the measurements was recorded as the crush strength. The crush strength test was deemed accurate to within ±25 g.

The pellets of Example 1 had a crush strength of 577 grams immediately after manufacture, 624 grams after 4 days, and 738 grams after 21 days. The pellets were visually observed to disperse within 24 hours of the introduction to a quantity of water.

Examples 1A, 2 & 3

These Examples illustrate the effect of adjusting the composition of the binder used to prepare the pest control composition and the equipment used to prepare the composition.

Example 1A was formulated using the same ingredients and ratios as in Example 1, but this Example was practiced on a pilot scale California pellet mill (model 399075). Approximately the same conditions of blending moisture and temperature were employed. For examples 2 and 3, the formulation was varied, as set forth below.

Example 1A

| | | |
|---|---|---|
| Porous starch absorbent | 1020 gm | 45% |
| Ethoxylated alcohol active agent | 227 gm | 35% |
| Urea-formaldehyde resin binder | 227 gm | 5% |
| Calcium lignosulfonate binder | 113.5 gm | 5% |
| Wheat middlings | 227 gm | 10% |

Example 2

| | | |
|---|---|---|
| Porous starch absorbent | 1020 gm | 45% |
| Ethoxylated alcohol active agent | 227 gm | 35% |
| Urea-formaldehyde resin binder | 91 gm | 4% |
| Calcium lignosulfonate binder | 136 gm | 6% |
| Wheat middlings | 227 gm | 10% |

Example 3

| | | |
|---|---|---|
| Porous starch absorbent | 1020 gm | 45% |
| Ethoxylated alcohol active agent | 227 gm | 35% |
| Urea-formaldehyde resin binder | 68 gm | 3% |
| Calcium lignosulfonate binder | 159 gm | 7% |
| Wheat middlings | 227 gm | 10% |

Following the procedure outlined in Example 1, the following crush strengths were recorded:

| Example | Crush Strength (4 days) (g) | Crush strength (11 days) (g) |
|---|---|---|
| Example 1 (pilot) | 503 | 546 |
| Example 2 | 346 | 478 |
| Example 3 | 320 | 383 |

The crush strength of Example 3 was below the 500 g desired minimum value, but this product is deemed suitable for use in certain applications.

The crush strength of the pilot scale example 1 differs from that of the production scale Example 1. This difference is believed to result from differences in processing conditions and equipment, and may be attributed to the limitations of and margin of error in the test. From the data, it is observed that the product of Example 2 has a somewhat better crush strength than that of Example 3, particularly after 11 days. The product of Example 1A had better crush strength. All of the products crush strengths improved with time.

It is thus seen that reducing the amount of the urea-formaldehyde resin binder while increasing the amount of the calcium lignosulfonate binder makes a softer pellet that more readily disperses in water. Alternatively, increasing the proportion of the urea-formaldehyde while reducing the calcium lignosulfonate has the opposite effect; the pellets are harder but slower to disperse.

Examples 4-8 were provided to illustrate the affect of varying the components of the pest control composition. All were prepared on a pilot scale California pellet mill under the same general conditions previously specified All of the products, except that of Example 7, had satisfactory crush strengths.

Example 4

The following pest control composition was prepared:

| | | |
|---|---|---|
| Porous starch absorbent | 1020 gm | 45% |
| Ethoxylated alcohol active agent | 227 gm | 35% |
| Urea-formaldehyde resin binder | 113.5 gm | 5% |
| Calcium lignosulfonate binder | 113.5 gm | 5% |
| Celite (diatomaceous earth) | 227 gm | 10% |

Celite filter aid, a diatomaceous earth material commonly used as an absorbent, was employed as a filler.

The pellets were found to have a crush strength of 701 grams after 7 days.

Example 5

The following pest control composition was prepared:

| | | |
|---|---|---|
| Porous starch absorbent | 680 gm | 30% |
| Ethoxylated alcohol active agent | 227 gm | 35% |
| Urea-formaldehyde resin binder | 113.5 gm | 5% |
| Calcium lignosulfonate binder | 113.5 gm | 5% |
| Celite (diatomaceous earth) | 567.5 gm | 25% |

The pellets were found to have a 7 day crush strength of 818 grams.

Example 6

The following pest control composition was prepared:

| | | |
|---|---|---|
| Porous starch absorbent | 1020 gm | 45% |
| Ethoxylated alcohol active agent | 227 gm | 35% |
| Urea-formaldehyde resin binder | 113.5 gm | 5% |
| Calcium lignosulfonate binder | 113.5 gm | 5% |
| Wood flour | 227 gm | 10% |

The pellets were found to have a 7 day crush strength of 1276 grams.

Example 7

The following pest control composition was prepared:

| | | |
|---|---|---|
| Porous starch absorbent | 963 gm | 42.5% |
| Ethoxylated alcohol active agent | 259 gm | 40% |
| Urea-formaldehyde resin binder | 113.5 gm | 5% |
| Calcium lignosulfonate binder | 113.5 gm | 5% |
| Celite (diatomaceous earth) | 170 gm | 7.5% |

The pellets were found to have a crush strength of 237 grams after 7 days.

Example 8

The following pest control composition was prepared:

| | | |
|---|---|---|
| Porous starch absorbent | 1020 gm | 45% |
| Ethoxylated alcohol active agent | 259 gm | 40% |
| Urea-formaldehyde resin binder | 113.5 gm | 5% |
| Celite (diatomaceous earth) | 227 gm | 10% |

The pellets were found to have a crush strength of 464 grams after 7 days.

It is thus seen that a pest control composition, a method for preparing a pest control composition, and a method for controlling pests are accomplished in accordance with the foregoing teachings.

While particular embodiments of the invention have been described above, the invention is not limited thereto, and it is contemplated that other pest control compositions, other methods for controlling a pest, and other methods for preparing a pest control composition are possible. The description herein of preferred embodiments and of exemplary embodiments should not be construed as limiting the invention in scope. Similarly, no unclaimed language should be deemed to limit the invention in scope. The invention is deemed to be defined by the full scope of the following claims, including without limitation any equivalents that may be accorded under applicable law.

What is claimed is:

1. A pest control composition comprising:
a partially hydrolyzed porous granular starch;
30 to 50 percent pest control agent absorbed within said porous starch, said pest control composition comprising an oleaginous material that is film-forming on a water surface;
a urea-based binder and a sulfonated lignin binder;
said pest control composition being in the form of discrete plural particles of a compressed mixture, said particles comprising pellets produced in a pellet mill, the partially hydrolyzed porous granular starch and binders included in amounts effective to provide said particles with a crush strength of at least 300 grams, wherein the crush strength is measured by selecting a sample pellet from said pellets and applying a force of compression at a speed of 1.0 mm/second and determining the force of compression at which the pellet cracks and breaks, the amounts of the partially hydrolyzed porous granular starch and the binders also effective to provide said particles with a release characteristic effective to release at least 50 percent of the pest control agent within 24 hours of the introduction of the pest control composition to a water column at 25° C.

2. The pest control composition according to claim 1, wherein the pest control composition further comprises a filler that is effective as a secondary absorbent.

3. The pest control composition according to claim 2, wherein the pest control composition includes 35 to 65 percent of a combination of partially hydrolyzed granular starch and filler that is effective as a secondary absorbent.

4. The pest control composition according to claim 1, wherein the pest control composition includes 5 to 15 percent binders.

* * * * *